Figure 1:
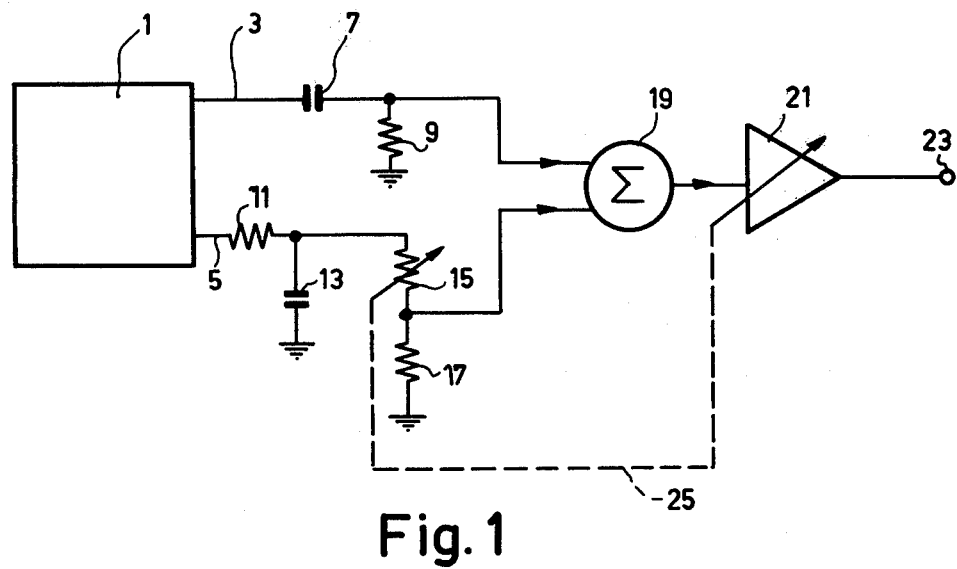

United States Patent [19]

Crestas et al.

[11] 4,161,173
[45] Jul. 17, 1979

[54] BLOOD PRESSURE GAUGE

[75] Inventors: Hans Crestas, Regensdorf; Edwin Zimmerman, Ostermundigen, both of Switzerland

[73] Assignee: U.S. Philips Corporation, New York, N.Y.

[21] Appl. No.: 731,338

[22] Filed: Oct. 12, 1976

[30] Foreign Application Priority Data

Oct. 17, 1975 [NL] Netherlands ......................... 7512187

[51] Int. Cl.² .............................................. A61B 5/02
[52] U.S. Cl. ................................................... 128/672
[58] Field of Search ............ 128/2 L, 2.05 A, 2.05 E, 128/2.05 M, 2.05 R, 2.05 T, 2.05 Q, 2.1 R, 2.06 B; 330/11; 328/127, 158, 177

[56] References Cited

U.S. PATENT DOCUMENTS

| 3,412,729 | 11/1968 | Smith | 128/2 L |
| 3,658,060 | 3/1972 | Eklof | 128/2.05 A |
| 3,915,156 | 10/1975 | Wastl | 128/2.05 E |
| 3,998,550 | 12/1976 | Konishi et al. | 128/2 L |
| 4,023,563 | 5/1977 | Reynolds et al. | 128/2.05 R |

OTHER PUBLICATIONS

Berne, R. M. et al., "Cardiovascular Physiology", pp. 76, 78-82, C. V. Mosby & Co., St. Louis, Mo. 1972.
"Blood Pressure Measuring"—L. J. Fiegel, Jr., IBM Tech. Discl. Bulletin, vol. 8, No. 6, Nov. 1965, p. 871.

Primary Examiner—Robert W. Michell
Assistant Examiner—Francis J. Jaworski
Attorney, Agent, or Firm—T. A. Briody; Bernard Franzblau

[57] ABSTRACT

A device for measuring blood pressure comprising a circuit having two signal paths one of which can guide the alternating current components and the other of which can guide the direct current component of the blood pressure signal, said signal paths comprising amplification and/or attenuation members so that the mutual ratio of the alternating current components and the direct current component is varied. The device furthermore comprises a summing device to recombine the two previously treated parts of the blood pressure signal and an amplifier or attenuator to make the overall amplification of the direct current component (average value) equal to unity.

4 Claims, 4 Drawing Figures

BLOOD PRESSURE GAUGE

The invention relates to a device for measuring blood pressure comprising a measuring part for forming an electrical blood pressure signal dependent on the blood pressure value.

The measuring part or device generally comprises a transducer which converts the blood pressure into an electrical signal and an amplifier to make the blood pressure signal suitable, for example, for an oscillograph or a recording device. Both the average value and the shape of the blood pressure curve made visible in this manner provide valuable information which enable the physician to make a diagnosis.

It has been proven in practice that the physician often feels the need of being able to study the variations in the blood pressure on an enlarged scale so as to be able to better study certain details. At the same time it is of importance that the average value of the displayed curve and the zero point remain unvaried. As a result of this it is not possible to simply amplify the blood pressure signal a number of times so as to more clearly show the fluctuations. In that case, actually, the whole curve would land in a different place on the display screen or recording paper.

It is an object of the invention to provide a device in which it is possible to display on an enlarged scale the variations in the blood pressure while the location of the blood pressure curve on the display screen or the recording paper does not vary substantially. The scale division on the screen or recording paper hence remains unvaried but the amplitude of the blood pressure variation apparently increases. For that purpose, the device according to the invention is characterized in that a circuit is present at the output of the measuring device which is designed to amplify the alternating current components of the blood pressure signal and to pass on the direct current components in a substantially unvaried manner.

The circuit arrangement preferably comprises two separate signal paths the first of which is designed to pass on the alternating current components of the blood pressure signal and the second of which is designed to pass on the direct current component of the blood pressure signal, at least one of the said signal paths comprising amplification and/or attenuation members which are adjusted so that more amplification and/or less attenuation, respectively, occur in the first signal path than in the second, said signal paths being connected to a summing device for forming a sum signal.

A very simple embodiment of the device according to the invention is characterized in that the first signal path is designed to pass alternating current signals in a substantially unchanged manner, that the second signal path comprises an attenuator which attenuates by a given factor the signals guided through said signal path, and that an amplifier is present which is designed to amplify the sum signal by the same factor. The said factor is preferably adjustable.

Figure 2:
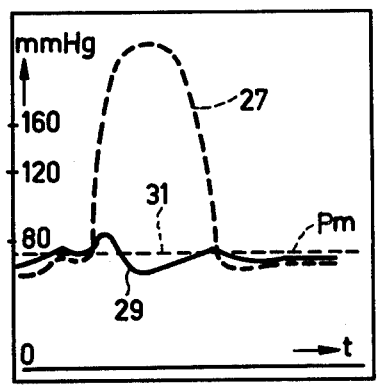
Figure 3:
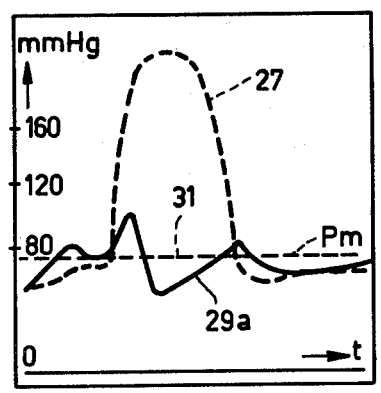
Figure 4:
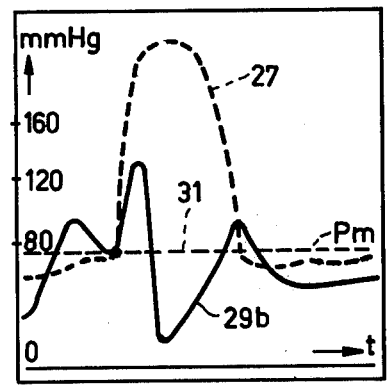

The invention will be described in greater detail with reference to the accompanying drawing in which FIG. 1 is a block diagram of an embodiment of a device according to the invention, and FIGS. 2 to 4 show three examples of recordings of blood pressure curves obtained by means of the device shown in FIG. 1.

The device shown in FIG. 1 comprises a measuring part 1 which may consist of a known commercially available blood pressure gauge. One suitable blood pressure meter is shown in U.S. Pat. No. 3,937,214. The measuring part 1 comprises in general a transducer for converting the blood pressure into an electrical signal as well as an amplifier and possibly calibrating and correction circuits.

Two separate signal paths 3, 5 are present at the output of the measuring part 1. The first signal path 3 comprises a network consisting of a series capacitor 7 and a grounded resistor 9 which passes only alternating current components, while the second signal path 5 comprises a network consisting of a series resistor 11 and a grounded capacitor 13 which forms the average value of the applied voltage and hence passes only the direct current component of the blood pressure signal. The second signal path 5 furthermore comprises an attenuating network consisting of a potentiometer formed by two resistors 15 and 17. The two signal paths 3 and 5 terminate in a summing device 19. The sum signal formed in said summing device is applied via an amplifier 21 to an output 23 which may be connected, for example, to an oscillograph or a recorder.

Both the attenuator 15, 17 and the amplifier 21 can preferably be controlled and their control members are preferably coupled together as is denoted by the dashed line 25. In this manner it can be achieved that the factor N by which the signal is attenuated by the attenuator 15, 17 is equal to the amplification factor of the amplifier 21 so that the signal guided via the second signal path 5 ultimately reaches the output 23 with its original amplitude. The signal which is guided via the first signal path 3 has experienced no or substantially no attenuation but is amplified by a factor N in the amplifier 21 so that the signal appearing at the output 23 consists of the original average value of the blood pressure signal produced by the measuring part 1 and, superimposed thereon, the variations of said blood pressure signal amplified by a factor N.

FIG. 2 shows a part of a recording of blood pressure curves obtained by means of the device according to FIG. 1. Two curves are visible, namely a curve 29 denoting the atrial pressure during a heart cycle and a curve 27 which indicates the ventricular pressure during the same period of time. The time is plotted on the horizontal axis and the amplitude (pressure in mm Hg) is plotted on the vertical axis. In FIG. 2 the two curves 27 and 29 have their original shape, that is to say that the amplification and attenuation factor N is equal to one. The curve 27, which may be used as a reference by the physician, also retains its original shape and amplitude in FIGS. 3 and 4. This curve is obtained by directly supplying the ventricular blood pressure signal from a blood pressure gauge 1 (or via a device as shown in FIG. 1, in which the factor N is always equal to unity) to an input of the recorder. The atrial blood pressure signal, however, has experienced a change in the recordings shown in FIGS. 3 and 4 in that the factor N in those cases was not equal to unity. In all cases the average value of the atrial blood pressure signal has remained the same (approximately 80 mm Hg). This value is shown as a straight line 31 in FIGS. 2 to 4. Actually said line will, of course, not appear separately under the recording unless special measures are taken for this purpose (e.g. the supply of the average value signal to an extra input of the recorder). In FIG. 3 the factor N is equal to two and in FIG. 4 N is equal to five. The atrial blood pressure curves 29a and 29b, respectively, in these figures, therefore show a ripple increased by said factors so that details of the shape of the curves can be carefully studied.

It will be obvious that embodiments other than that shown in FIG. 1 are possible. For example, instead of the attenuator 15, 17 in the second signal path 5 and the amplifier 21 after the summing device 19, an amplifier in the first signal path 3 may be used with or without an attenuator after the summing device. If an attenuator is used after the summing device, then a compensating amplifier may be included in the summing device. Combinations of the two solutions are also possible. The summing device 19 and the amplifier 21 may be combined, if desired. The circuit may also comprise an amplifier which is more negatively fed for direct current than for alternating current, the negative feedback coupling being preferably controllable. Some blood pressure gauges also provide, in addition to the blood pressure signal, a signal which indicates the average value of the blood pressure. In that case said signal may be supplied as such to the second signal path 5. The network 11, 13 is then superfluous.

What is claimed is:

1. A device for measuring blood pressure comprising a measuring device for forming an electrical blood pressure signal dependent on the blood pressure value, said electrical blood pressure signal containing alternating current components and a direct current component having a given mutual ratio determined by the subject under test, a circuit arrangement coupled to the output of the measuring device and comprising two separate signal paths and an output terminal wherein the first signal path is designed to selectively pass alternating current in a substantially unvaried manner, the second signal path comprising means for selectively passing the direct current component of the blood pressure signal and an attenuator which attenuates by a given factor the signals guided through said second signal path, a common output for the two signal paths at which a sum signal is produced, and an amplifier responsive to the sum signal and designed to amplify the sum signal by the same factor and to couple same to the output terminal to derive an output signal, the amplifier amplifying the alternating current components of the blood pressure signal relative to the direct current component and passing on the direct current component in a substantially unvaried manner thereby to form at the output terminal an output signal having a different said mutual ratio of alternating to direct current components but the same value of the direct current components.

2. A device as claimed in claim 1 wherein said attenuator is adjustable and the gain of the amplifier is adjustable so as to provide an overall unity gain factor for the direct current component of the blood pressure signal.

3. A device for measuring blood pressure comprising a measuring device for forming an electrical blood pressure signal dependent on the blood pressure valve, said electrical blood pressure signal containing alternating current components and a direct current component having a given mutual ratio determined by the subject under test, a circuit arrangement coupled to the output of the measuring device and comprising two separate signal paths and an output terminal wherein the first signal path is designed to selectively pass alternating current in a substantially unvaried manner, the second signal path comprising means for selectively passing the direct current component of the blood pressure signal and an attenuator which attenuates by a given factor the signals guided through said second signal path, a common output for the two signal paths at which a sum signal is produced, and an amplifier responsive to the sum signal and designed to amplify the sum signal by the same factor and to couple same to the output terminal to derive an output signal, the amplifier amplifying the alternating current components of the blood pressure signal relative to the direct current component and passing on the direct current component in a substantially unvaried manner thereby to form at the output terminal an output signal having a different said mutual ratio of alternating to direct current components but the same value of the direct current components, and means for adjusting the attenuator and the amplifier gain in synchronism so as to provide an overall gain of the AC component along with an overall unity gain factor for the DC component of the blood pressure signal.

4. Apparatus for measuring blood pressure comprising a Geasuring device for deriving an electric blood pressure signal containing an AC component and a DC component in a given mutual ratio determined by the blood pressure of a subject, circuit means coupled to the output of the measuring device and including means for separating the blood pressure signal into individual AC and DC signal components, an output terminal coupled to said circuit means, the separating means of said circuit means comprising first and second separate signal paths for selectively passing the AC and DC signal components, respectively, of the blood pressure signal, said second signal path including attenuation means for altering the amplitude of the DC signal component by a given factor, said circuit means frther comprising an amplifier coupled to receive the AC and the DC signal components passed through said first and second signal paths thereby to increase the amplitude of the AC signal component relative to that of the DC signal component so as to alter said given mutual ratio and to pass the DC signal component substantially unchanged in amplitude, and means for adjusting the attenuation means and the amplifier gain in synchronism whereby the amplifier provides an overall gain for the AC signal component and the amplifier gain factor and the attenuation factor of the attenuation means are correlated so as to provide an overall unity amplification factor for the DC signal component, an output signal being produced at said output terminal having an AC and a DC signal component wherein said given mutual ratio is changed but the value of the DC signal component is the same.

* * * * *

UNITED STATES PATENT AND TRADEMARK OFFICE
CERTIFICATE OF CORRECTION

PATENT NO. : 4,161,173
DATED : July 17, 1979
INVENTOR(S) : Hans Crestas et al

It is certified that error appears in the above—identified patent and that said Letters Patent is hereby corrected as shown below:

Column 1, line 63, after "which" insert -- : --.

Claim 3, line 3, "valve" should read -- value --.

Claim 4, line 2, "Geasuring" should read -- measuring --.
line 15, "frther" should read -- further --.

Signed and Sealed this

Sixteenth Day of September 1980

[SEAL]

Attest:

SIDNEY A. DIAMOND

Attesting Officer

Commissioner of Patents and Trademark